US012342986B2

(12) United States Patent
Chung et al.

(10) Patent No.: US 12,342,986 B2
(45) Date of Patent: Jul. 1, 2025

(54) DEVICE FOR COLLECTION OF EXCESS FLUIDS FROM AN ENDOSCOPE

(71) Applicants: Waihong Chung, East Providence, RI (US); Paul Akerman, Providence, RI (US)

(72) Inventors: Waihong Chung, East Providence, RI (US); Paul Akerman, Providence, RI (US)

(*) Notice: Subject to any disclaimer, the term of this patent is extended or adjusted under 35 U.S.C. 154(b) by 103 days.

(21) Appl. No.: 17/371,171

(22) Filed: Jul. 9, 2021

(65) Prior Publication Data

US 2022/0047151 A1    Feb. 17, 2022

Related U.S. Application Data

(60) Provisional application No. 63/066,228, filed on Aug. 15, 2020.

(51) Int. Cl.
*A61B 1/00* (2006.01)

(52) U.S. Cl.
CPC ........ *A61B 1/00137* (2013.01); *A61B 1/0011* (2013.01)

(58) Field of Classification Search
CPC . A61B 1/00137; A61B 1/0011; A61B 1/0669; A61B 10/04; A61B 2017/2905; A61B 90/57; A61B 1/00131; A61B 1/00142; A61B 1/012; A61B 1/018; A61M 1/60; A61M 1/602; A61M 1/604; A61M 1/61; A61M 1/62; A61M 1/63; A61M 1/631; A61M 1/69; A61M 1/70; A61M 3/02; A61F 5/445

See application file for complete search history.

(56) References Cited

U.S. PATENT DOCUMENTS

| | | | | | |
|---|---|---|---|---|---|
| 3,810,503 | A | * | 5/1974 | Lewis, Jr. | A61J 1/10 383/96 |
| 5,769,794 | A | * | 6/1998 | Conlan | A61B 17/00234 600/562 |
| 2007/0203516 | A1 | * | 8/2007 | Nayak | A61B 17/32053 606/185 |
| 2009/0287111 | A1 | * | 11/2009 | Kaye | A61B 1/00137 600/101 |
| 2011/0251458 | A1 | * | 10/2011 | Terliuc | A61B 1/00082 600/116 |

FOREIGN PATENT DOCUMENTS

| | | | | |
|---|---|---|---|---|
| CN | 213046818 | * | 7/2020 | A61B 1/00 |
| CN | 213046818 U | * | 4/2021 | |
| WO | WO-2006089600 A1 | * | 8/2006 | A61F 5/44 |

OTHER PUBLICATIONS

CN213046818 English translation (Year: 2020).*

* cited by examiner

*Primary Examiner* — Aaron B Fairchild
*Assistant Examiner* — Megan Elizabeth Monahan
(74) *Attorney, Agent, or Firm* — Feeney IP Law; Daniel W. Sullivan; Alan F. Feeney (57) ABSTRACT

A device to safely collect any fluid discharged through the biopsy cap into another container without contaminating the surrounding environment. A device that can be attached to an endoscope in order to collect any fluid discharged through an external opening of an endoscope's internal channel.

20 Claims, 9 Drawing Sheets

DEVICE FOR COLLECTION OF EXCESS FLUIDS FROM AN ENDOSCOPE

This application claims benefit to a provisional application No. 63/066,228, filed on Aug. 15, 2020.

BACKGROUND OF THE INVENTION

1. Field of the Invention

The present invention relates generally to medical devices and medical instruments provided for and relating to inspection of internal cavities. Particularly, the present invention relates to endoscopes which can be introduced into a person's body to inspect internal cavities or lumens.

2. Description of the Prior Art

Modern endoscopes typically comprise a flexible tube with one or more internal channels that can be used to inject into or aspirated from the body air or fluids. Small instruments can also be passed into the body through one of these channels. Most modern endoscopes (e.g., side-viewing scopes, gastroscopes, and colonoscopes) feature a combined suction/instrument channel connected by a Y-shape connector internally near the handle portion of the instrument. A soft rubber seal, commonly known as a biopsy cap, is typically placed on top of the instrument insertion opening to maintain a negative pressure within the suction/instrument channel as well as to minimize overspill of fluids through the instrument insertion opening.

U.S. patent application Ser. No. 12/467,726, by Kaye, discloses a device for use with an endoscope. The body defines a vessel for collecting fluid that may otherwise escape through the port or valve of the endoscope.

SUMMARY OF THE INVENTION

Advantages and Differences of Invention Over Known Prior Art

Unfortunately, with current assemblies, the overspill of fluids from the instrument insertion opening through the biopsy cap remains a common occurrence in practice. This is especially common during procedures that require repeated passages of instruments leading to a loss of integrity of the biopsy cap. Additionally, this may also occur during procedures that utilize air insufflations resulting in a positive pressure gradient that forces fluids to escape from the biopsy cap.

As a term of art, 'overspill of fluids' is a polite way to describe the occurrence, however, this phrase does not refer to the spilling of water, or other sanitary fluids. Instead, this phrase refers to fluids such as bile, blood, liquid stool, or other bodily secretions. Being spilled during testing, these fluids may understandably contain known or unknown pathogens. As a result, any overspill of fluids is problematic for many reasons beyond the mess that is created by fluid escaping the biopsy cap. During a procedure the risks presented by an overspill of fluids are increased. Specifically, an overspill of fluids at this time not only leads to contamination of the procedure area but also poses significant health risks to the endoscope operator.

Therefore, there exists a need for a device to safely collect any fluid discharged through the biopsy cap into another container without contaminating the surrounding environment. The present invention seeks to address this need and fulfills other goals and objectives as well. One embodiment of the present invention relates to a device that can be attached to an endoscope in order to collect any fluid discharged through an external opening of an endoscope's internal channel.

It is an object of the present invention to provide a fluid container for collecting fluids discharged from an endoscope. The endoscope usually has at least one instrument and at least one instrument channel. The fluid container has a front wall, a rear wall, a bottom wall, and side walls. The front wall, rear wall, bottom wall, and side walls are waterproof and define an interior portion of the fluid container.

The fluid container also has an expandable collection section which is also defined by the front wall, rear wall, bottom wall, and side walls. The expandable collection section is capable of expanding such that the fluid container can alter shape from a first configuration to a second configuration.

The fluid container also has at least two openings. The first opening is provided to facilitate insertion of the at least one instrument into the fluid container. The first opening is usually located on the front wall of the fluid container.

The second opening is provided to facilitate egression of the at least one instrument inserted through the first opening to now exit the fluid container. Because the second opening is adapted to fit over the at least one instrument channel of the endoscope, this enables the second opening to facilitate egression of the at least one instrument into the at least one instrument channel of the endoscope.

It is an object of the present invention to provide the fluid container with walls which are substantially transparent so that the interior portion can be visualized from outside the fluid container.

It is another object of the present invention to provide the fluid container with a marker located around the first opening. This marker should be capable of providing a visual and tactile target to help a user identify the orifice of the first opening.

It is a further object of the present invention to provide the fluid container with a spill-proof seal which can cover the orifice of the first opening to facilitate reduction of overspill of fluids through this first opening.

It is yet another object of the invention to provide the fluid container with a self-adhesive band around the second opening as a means for attaching the apparatus to an endoscope. The fluid container may also have an integrated rubber seal around the second opening to connect the fluid container to the instrument channel on an endoscope. The fluid container may also have a third opening, which permits fluids collected within the fluid container to be removed, the third opening located adjacent the bottom wall of the fluid container.

The fluid container may also have a third opening and a water-tight sealing mechanism, such as a zipper, connected to the third opening. The zipper would be capable of facilitating the third opening in opening and securely closing repeatedly. The fluid container may also have the front wall, rear wall, bottom wall, and side walls made of waterproof materials such as plastic, silicone, rubber, or cellulose.

The present invention achieves these and other objectives by providing a fluid container for collecting fluids discharged from an endoscope. The endoscope has at least one instrument and at least one instrument channel. The fluid container has at least one folded waterproof wall defining an interior portion of the fluid container.

The fluid container has an instrument insertion opening which is adapted to facilitate insertion of the at least one instrument therethrough into the fluid container, the instrument insertion opening which is located on an exterior facing portion of the water-proof wall of the fluid container.

The fluid container has an endoscope attachment aperture which is adapted to be fitted over the at least one instrument channel of the endoscope. The endoscope attachment aperture is adapted to facilitate egression of the at least one instrument, inserted through the first opening, to exit the fluid container and enter the at least one instrument channel of the endoscope.

The fluid container has an expandable collection section which is capable of collecting the fluids discharged from the at least one instrument channel of the endoscope. The fluid container also has a first packing configuration having a first volume, and a second collecting configuration having a second volume. The first volume of the first packing configuration is less than the second volume of the second collecting configuration. The second volume of the second collecting configuration may be at least five times larger than the first volume of the first packing configuration.

DETAILED DESCRIPTION OF THE INVENTION

To promote an understanding of the principles of the invention, reference will now be made to the embodiment illustrated in the drawings and specific language will be used to describe the same. It will nevertheless be understood that no limitations of the scope of the invention are thereby intended. Such alterations and further modifications in the illustrated device, and such further applications of the principles of the inventions as illustrated herein being contemplated as would normally occur to one skilled in the art of which the invention relates.

Figure 1:
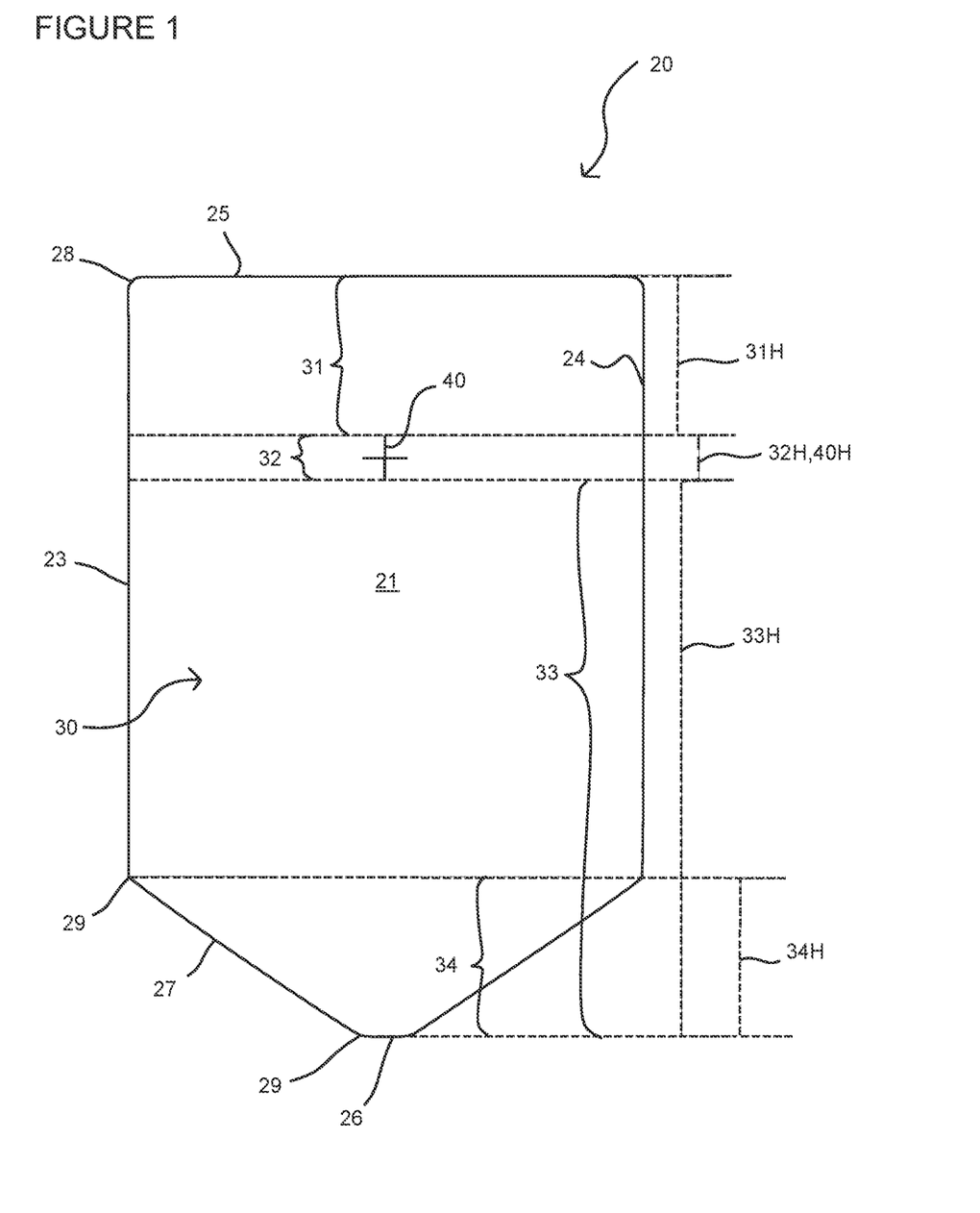
FIG. 1 is a front view of a preferred embodiment of the present invention.
Figure 2:
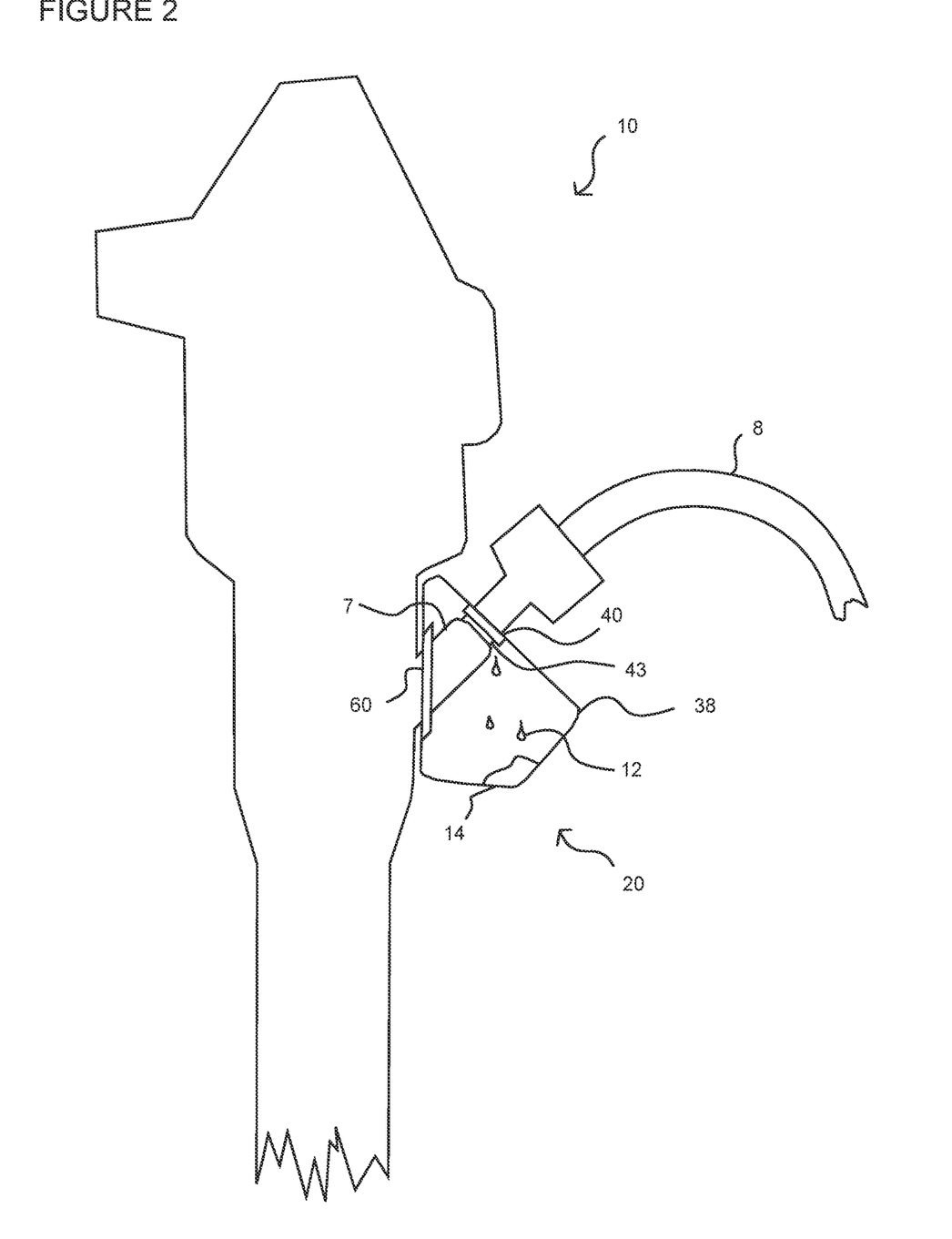
FIG. 2 is a side view of one transparent embodiment, shown in the second use configuration, during use and attached to an endoscope.

One embodiment of the invention is illustrated in FIG. 1 through FIG. 2. In each of the embodiments discussed, a fluid container 20 according to the present invention has three main components: a spill-proof instrument insertion opening 40, an endoscope attachment aperture 60, and a collection section 30. As can be seen in FIG. 2, the spill-proof instrument insertion opening 40 is located on the front wall 21 of the fluid container 20 and the endoscope attachment aperture 60 is located on the back wall 22 (opposite the front wall 21) of the fluid container 20. The fluid collection section 30 is the void defined by the walls of the fluid container 20 and extends between the front and back walls 21, 22.

Fluid Container 20 with Adaptable Configurations

Rather than designing a fluid container 20 as an immutable shape incapable of adaptable configurations like the prior art, the present invention is capable of at least three configurations. These alternative adapting configurations facilitate easy storage, maneuverability, and portability. Specifically, these configurations enable the fluid container to be collapsible so that the device can be easily stored flat when folded.

Figure 1A:
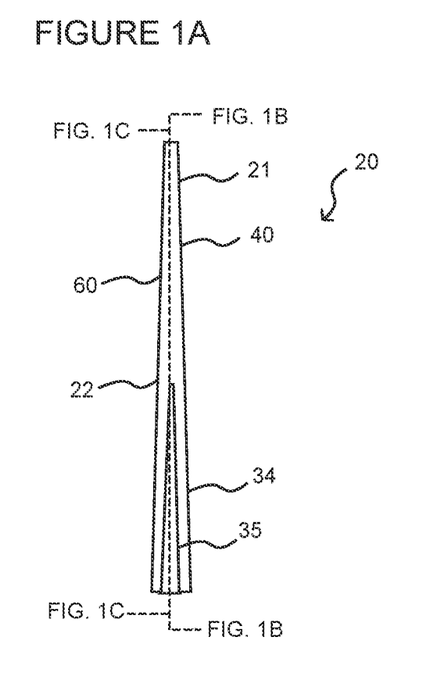
FIG. 1A is a side view of a first packing configuration of the embodiment shown in FIG. 1.

In order to easily facilitate folding, storing, and unfolding from a first folded configuration (FIG. 1A) to at least a second use configuration (FIG. 1D), the expandable collection section 34 has a foldable portion 35 generally comprised of portions of the side walls 23, 24, angled side walls 27, and the bottom wall 26.

Fluid container 20 can be manufactured from plastic, silicone, or any other flexible and water-proof materials. The thickness of the material may be between 0.25 mm and 5 mm, preferably at least between 0.5 mm and 3 mm, and typically between 0.5 mm and 1 mm.

Figure 1B:
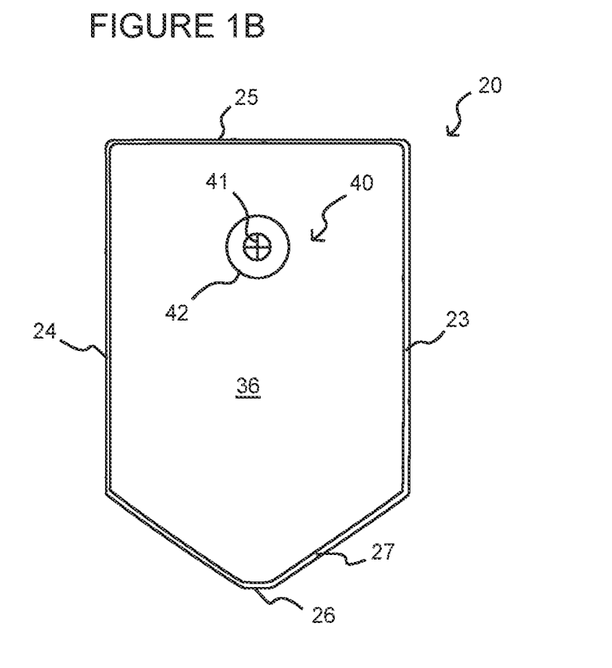
FIG. 1B is a cross-sectional view of the front of the embodiment shown in FIG. 1.
Figure 1C:
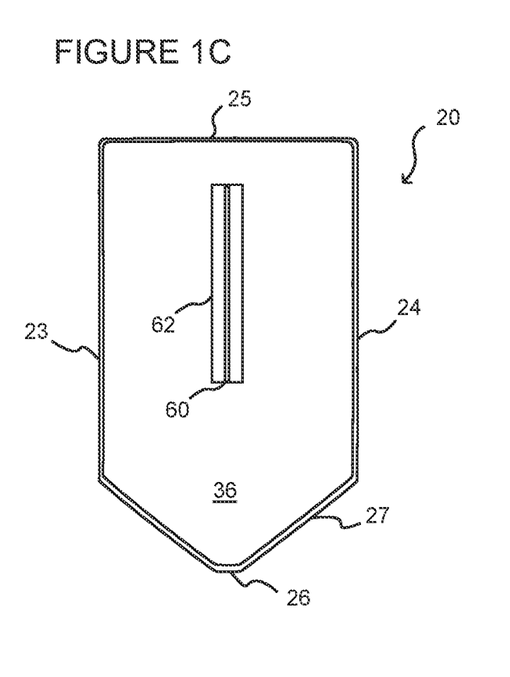
FIG. 1C is a cross-sectional view of the rear of the embodiment shown in in FIG. 1.

For clarity, the present invention is depicted in the accompanying drawings as if the material was completely opaque so as to distinguish between elements present in different positions. Ideally however, the material of the fluid container 20 comprising the front, back, left, right, top and bottom walls 21, 22, 23, 24, 25, 26, 27 should be clear, semi-transparent, or fully transparent material 38 so that the amount of fluid content 12 can be easily visualized from an outside perspective. When transparent material is employed, internal components, such as are visible in FIGS. 1B and 1C, are also fully visible from an external perspective.

Also, while the terms front, side, rear, back and top are used to refer to the water-proof walls of the container 20, these terms are used solely for ease of discussion. Indeed, in this embodiment, the walls are entirely integral with one another, formed from a single sheet of thin layer of medical grade plastic sheeting by folding along multiple edges and sealing along two edges.

Fluid Collection Sections 30

While the invention places no limitations on the holding size of fluid container 20, the collection section 30 should be large enough to hold the anticipated amount of fluid, but not so large so as to interfere with the normal operation of the endoscope.

While many various shapes for the fluid container 20 are possible, most embodiments have an expandable collection section 34 which has an expanding triangular prism shape. In these circumstances, the portion above the expandable collection section 34 also usually has an upper triangular prism shape. The height of the upper triangular prism 39 is the height 31H of the upper portion 31 plus the height 32H of the biopsy section 32 plus the height 33H of the main section 33 minus the height 34H of the expanding collection section 34.

In the second and first configurations, the height 20h of the container 20 may be between 30 mm and 200 mm, and typically around 150 mm. The height 31H of the upper section 31 may be between 20 mm and 80 mm, preferably at least between 50 mm and 60 mm, and typically around 55 mm. The height 32H of the biopsy section 32 may be between 2 mm and 12 mm, preferably at least between 5 mm and 10 mm, and typically around 8 mm.

The height 33H of the main section 33 may be between 20 mm and 90 mm, preferably at least between 40 mm and 70 mm, and typically around 60 mm. The height 34H of the collection section 34 may be between 10 mm and 80 mm, preferably at least between 20 mm and 60 mm, and typically around 40 mm.

Generally, the height 32H (and corresponding volume) of the biopsy section 32 will be less than the height 31H (and corresponding volume) of the upper section 31. The height 31H (and corresponding volume) of the upper section 31 will generally be less than the height 33H (and corresponding volume) of the main section 33.

Figure 1D:
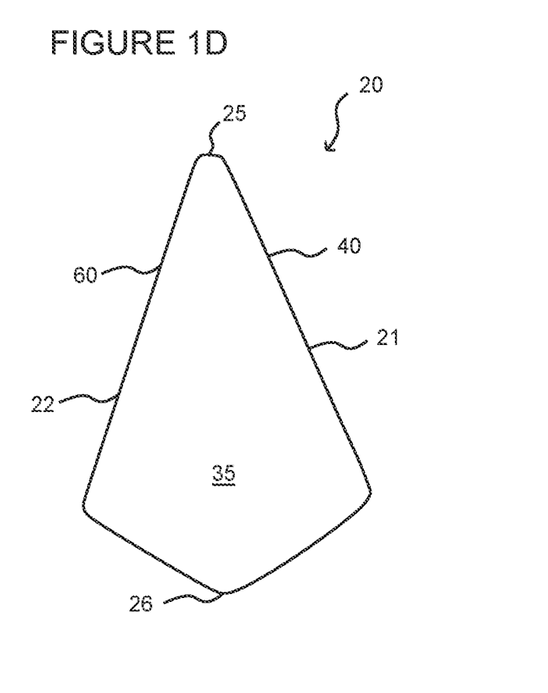
FIG. 1D is the side view of the embodiment shown in FIG. 1A, now in a second use configuration.

The depth of the container 20 alters between the first configuration (FIG. 1A) and the second configuration (FIG. 1D). Specifically, in the first configuration, the depth of the container 20 is typically about 5 mm. In the second configuration, the depth of the container 20 varies between 5 mm along the top of the upper section 31 and expanding to 80 mm at the widest portion of the collection section 34.

Specifically, in the second configuration, the depth 31d of the upper section 31 may expand from 2 mm to 50 mm, preferably at least from 4 mm to 40 mm, and typically from 5 mm to 20 mm. The depth 32d of the biopsy section 32 may expand from 10 mm to 50 mm, preferably around from 15 mm to 40 mm, and typically from 20 mm to 30 mm. The depth 33d of the main section 33 may expand from 20 mm to 70 mm, preferably around from 25 mm to 60 mm, and typically from 30 mm to 55 mm. At its greatest depth 34d, the collection section 34 may be between from 60 mm to 100 mm, preferably at least between 60 mm to 80 mm, and typically around 70 mm.

In the first configuration, the fluid container 20 is a simple rectangle plus two matching triangles, so volume of the fluid container 20 may be calculated simply from $V_1 = ((W_{39}*H_{39}*D_{39}) + 2*(½*W_{34}*H_{34}*D_{34})) =$ (width*height*depth). For a fluid container 20 with measurements of $20W=70$ mm, $20D_1=1$ mm and $20H=160$ mm, then the volume $V_1=11.2$ mL.

In the second configuration, the volume of the lower collection section 34 in the second use configuration will generally be greater than the volume of the remainder of the container 20 regardless of a ratio of height 34h in correlation with height 33h, or stated mathematically, $V_{34}>(V_{30}-V_{34})$ or $V_{34}>V_{39}$.

The significantly larger volume size in the second configuration is possible due to the altered shape in the second configuration. The volume of the entire fluid container 20 may be determined by finding the volume of the two triangular prism shapes defining the fluid container. However, as previously stated, to ensure that no fluids are lost, it is preferable that only the portion of the fluid container 20 below the insertion opening 40 is considered viable for fluid collection. Mathematically then, the volume of the container in the second configuration can be determined from:

$$V_2 = (½\ w*h*d)_{39} + (½\ w*h*d)_{34} - (½\ w*h*d)_{31}$$

For a container 20 with measurements $20W=70$ mm, $20H-31H-32H=120$ mm, $20D=70$, $33H-34H=40$, $31H+32H=25$, $26D=70$, and then $V_2=(½*70*120*70)+(½*70*40*70)-(½*70*25*70)=331$ mL. Overall, the main section 33 (including the collection section 34) of a fluid container 20 in the second configuration may contain between 100 cc to 450 cc, or preferably between 150 cc to 400 cc, while 250 cc to 350 cc in size should be adequate for a typical application.

Returning then to our example, it is possible to compare the volume of the container 20 in the first configuration, $V_1$, to the volume of the container 20 in the second configuration, $V_2$, where $V_1=56$ mL and $V_2=331$ mL, $V_2 = \tilde{}(V_1*6)$. For this embodiment then, the volume of the container 20 in the second configuration, $V_2$, is more than 5 times the volume of the container 20 in the first configuration, $V_1$. For other embodiments the volume of the container 20 in the second configuration, $V_2$, is at least 4 times the volume of the container 20 in the first configuration, $V_1$. In yet further embodiments, the volume of the container 20 in the second configuration, $V_2$, is between 2 to 10 times the volume of the container 20 in the first configuration, $V_1$.

Spill-Proof Instrument Insertion Opening 40

Figure 3:
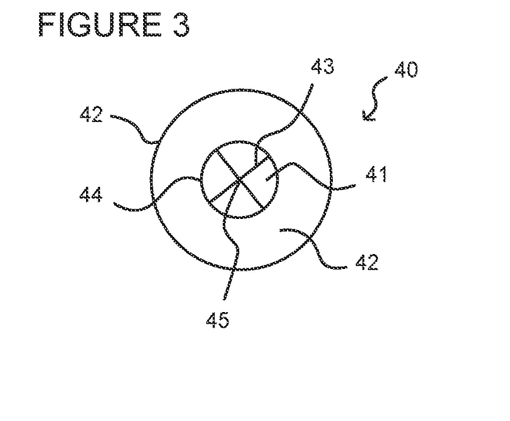
FIG. 3 is an enlarged front view of a spill-proof instrument insertion opening according to one embodiment of the invention.

Spill-proof instrument insertion opening 40 is affixed to a front side of the fluid container 20, such that the orifice of the opening is positioned right above the biopsy cap 67 when the device is properly attached to an endoscope 10, as illustrated in FIG. 2. FIG. 3 illustrates an enlarged view of one embodiment of spill-proof instrument insertion opening 40. The instrument insertion opening 40 is composed of an outer ring 42 and an inner fenestrated membrane 41.

The instrument insertion opening 40 is adapted to facilitate insertion of the endoscope instrument (or tool) through the opening 40 into the fluid container 20. To facilitate this, directionality, the instrument insertion opening 40 is located on an exterior facing portion of the water-proof wall of the fluid container 20.

The outer ring 42 can be manufactured from rubber, foam, or any other semi-flexible and water-resistant materials. The purpose of outer ring 42 is to maintain the integrity of inner fenestrated membrane 41. In embodiments having a transparent wall 38, the visually distinct coloring of the outer ring 42 also provides a visual and tactile target to help an endoscope operator locate the inner fenestrated membrane 41 easily and efficiently during a procedure. The inner diameter 43 of outer ring 42 should match the size of a typical biopsy cap, may be between 5 mm and 20 mm, preferably at least between 8 mm and 12 mm, and typically around 10 mm. The outer diameter 44 of outer ring 42 may be between 10 mm and 40 mm, preferably at least between 15 mm and 30 mm, and typically around 20 mm.

The inner fenestrated membranes 41 acts as flexible valve walls which engage the side walls of the endoscope instrument to reduce fluid back flow. The insertion opening 40 may contain one or more layers of fenestration membrane in order to provide adequate spillage resistance. Indeed, in the embodiment shown in FIG. 3, a second layer of fenestration membranes is present with a fenestration pattern 43 that is at an angle to the first layer of fenestration membrane as shown in FIG. 1. Specifically, the fenestration patterns in FIG. 1 are vertical and horizontal, while the fenestration patterns 43 of the additional layer of membranes 41 in FIG. 3 are rotated at 45 degrees with respect to the first layer.

The fenestration patterns 43 of both the first and second layer of membranes 41 extend from the inner diameter 44 of the outer circle 42 until reaching an internal axis 45. The fenestration patterns 43 shown here causing portions of the membranes 41 to have a cuneate, triangular, wedge or petal shape. These membranes 41 can be manufactured from the same material as fluid container 20 or any other flexible and water-proof materials.

Figure 5:
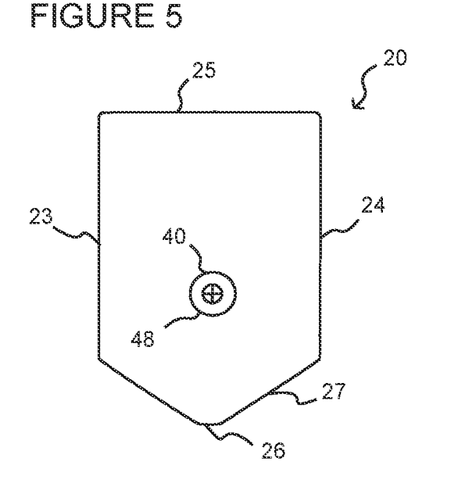
FIG. 5 is a front view of another embodiment of the invention with an alternative spill-proof instrument insertion opening and an integrated biopsy cap.

As illustrated in FIG. 2, in some embodiments, the spill-proof instrument insertion opening 40 is not attached to the biopsy cap. A small gap 43 exists between spill-proof instrument insertion opening 40 and the biopsy cap 7. This separation 43 facilitates in reducing or abolishing the capillary effect that would otherwise occur due to the small internal diameter of the suction instrument channel and facilitates easier intentional draining of the fluids 12 into fluid container 20 when desired. FIG. 5 shows an alternative embodiment of the fluid container 20 of the present invention having an alternative position for the spill proof instrument insertion opening 40.

Endoscope Attachment Aperture 60

Endoscope attachment aperture 60 is affixed to the back side of fluid container 20 opposite from spill-proof instrument insertion opening 40, as illustrated in FIG. 2. Endoscope attachment aperture 60 provides an orifice 61 through which the instrument insertion opening 40 of an endoscope 10 and the biopsy channel 7 are connected to fluid container 20. It also serves as an attachment point to help secure the fluid container 20 around the handle of an endoscope 10.

Specifically, the endoscope attachment aperture 60 is adapted to fit over the instrument channel 7 of the endoscope 10. The endoscope attachment aperture 60 facilitates egression of the endoscope instrument, previously inserted through the first opening, to exit the fluid container 20 and enter the instrument channel 7 of the endoscope 10.

Figure 4:
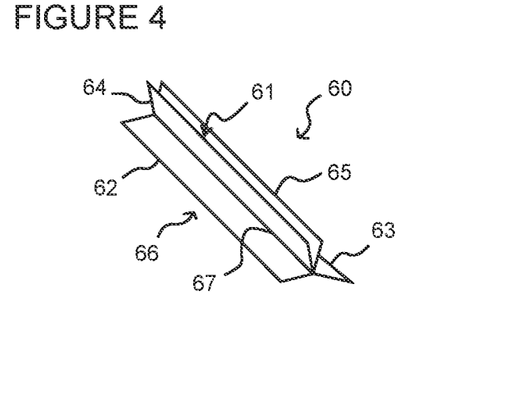
FIG. 4 is an enlarged perspective view of an endoscope attachment opening according to one embodiment of the invention.

FIG. 4 provides a view of one embodiment of endoscope attachment aperture 60. In this embodiment, the endoscope attachment aperture 60 has two strips of adhesive 62, 63 which are aligned next to each other. These strips 62, 63 extend lengthwise from a top end adjacent the top 25 of the container 20, to a bottom end adjacent the bottom 26 of the container 20.

In this embodiment, each strip 62, 63 is folded horizontally from side to side, usually along a midway point 67, such that wings 64, 65 extend outwardly from the folding point 67. These wings 64, 65 are extensions that run along the external sides of the biopsy cap (inside the fluid container 20) and can form a water-tight seal opposite the instrument insertion opening of an endoscope, as illustrated in FIG. 2.

The height of the orifice 61 may be between 5 mm and 70 mm, preferably at least between 10 mm and 40 mm, and typically around 25 mm.

Additional Embodiments

Other embodiments of the invention are illustrated in FIGS. 5-18. However, as the principle elements of these additional embodiments remain constant and similar to the previously discussed elements of the present invention, there is no need to repeat the discussion of these identical elements.

Integrated Biopsy Cap 67

Figure 6:
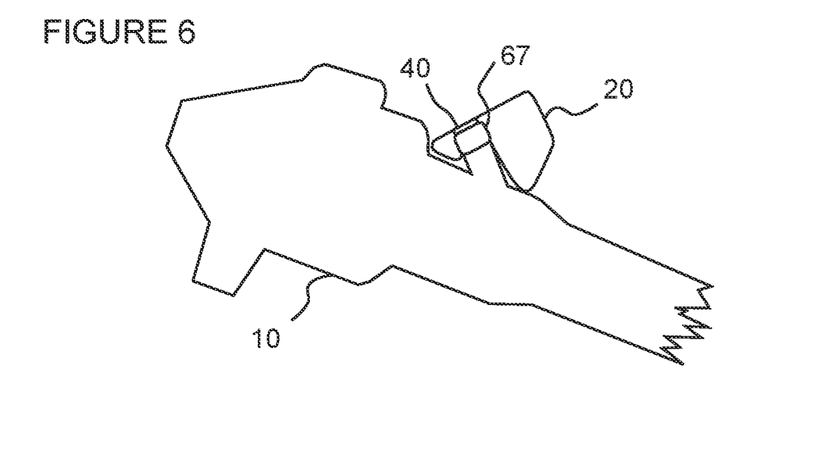
FIG. 6 is a side view of another preferred embodiment of the invention in the second use configuration when attached to an endoscope.
Figure 7:
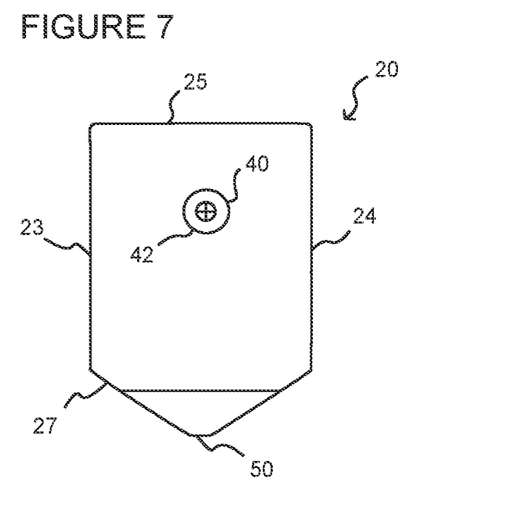
FIG. 7 is a front view of another preferred embodiment of the invention with a resealable drainage opening.
Figure 8:
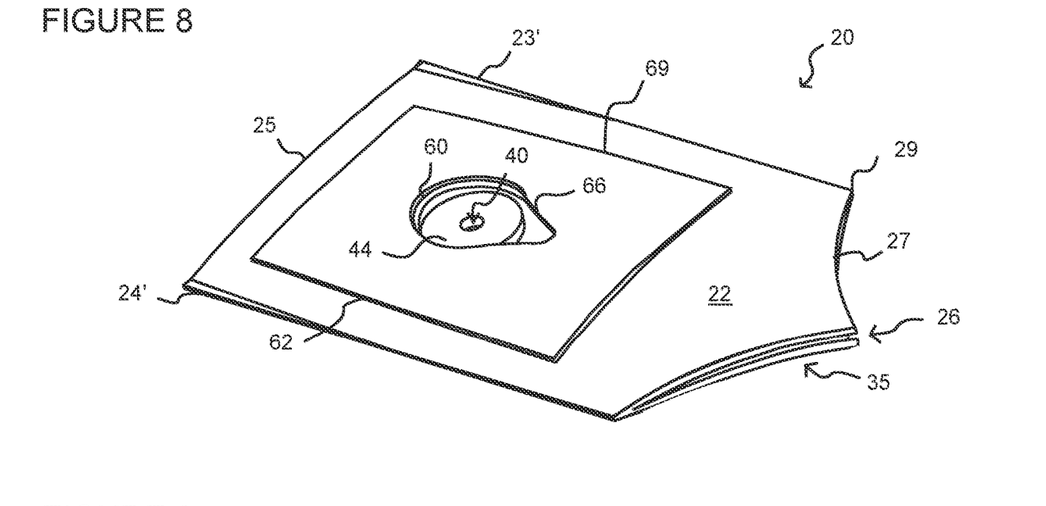
FIG. 8 is a rear side perspective view of another embodiment of the present invention in a first packing configuration.
Figure 9:
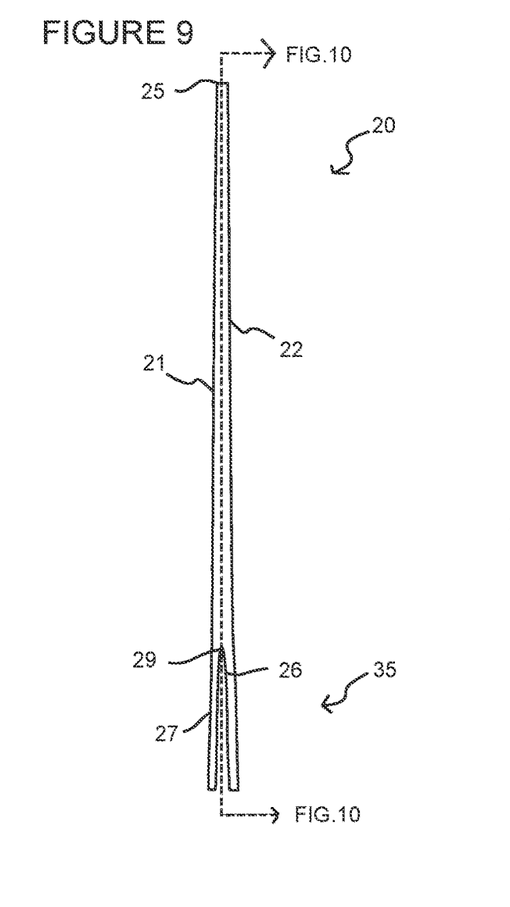
FIG. 9 is a side view of the first packing configuration of the embodiment shown in FIG. 8.
Figure 10:
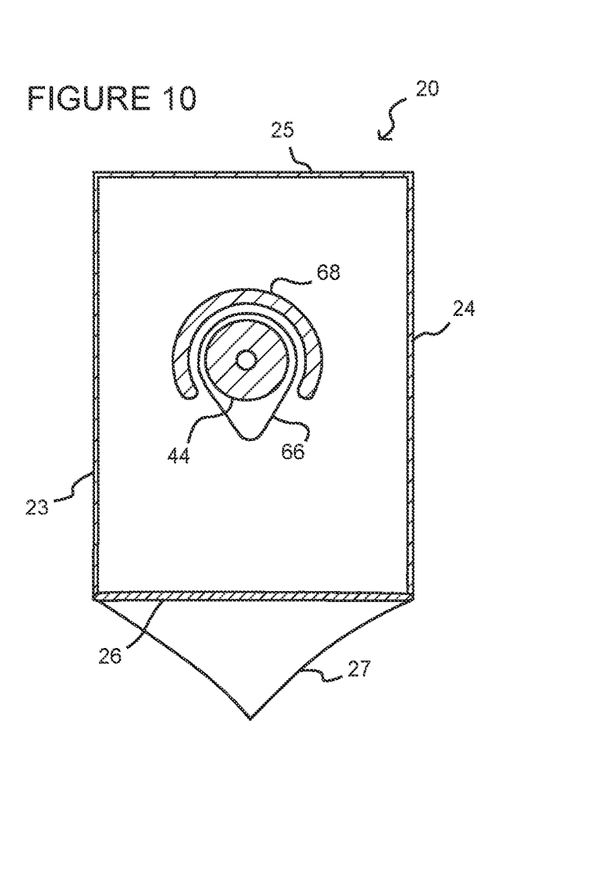
FIG. 10 is a cross-sectional view of the embodiment in FIGS. 8 and 9.

In the embodiment shown in FIGS. 6 and 7, the fluid container 20 has a spill-proof instrument insertion opening 40 on the front of fluid container 20 and an integrated biopsy cap 67 on the opposite rear side of fluid container 20. The construction of fluid container 20 and spill-proof instrument insertion opening 40 in this preferred embodiment is the same as discussed above.

Integrated biopsy cap 67 represents a soft rubber seal similar to that used for any commercially available biopsy cap. However, in the present embodiment, the integrated biopsy cap 67 is permanently bonded to fluid container 20, such that the integrated biopsy cap 67 can be properly aligned to spill-proof instrument insertion opening 40, as illustrated in FIG. 6.

Resealing Drainage Opening 50

Another embodiment of the invention is illustrated in FIG. 7. In this embodiment, a resealing drainage opening 50 is provided along the bottom wall 26 to correspond with the expandable collection section 34 of the fluid container 20. This resealable drainage opening 50 allows fluid collected in fluid container 20 to be emptied without removing the fluid container 20 from an endoscope. Resealing drainage opening 50 can be opened and closed repeatedly throughout the lifetime of the container 20. The resealing drainage opening 50 in this embodiment may be constructed based on a zipper, zip-seal, slider, or any other water-tight closure mechanisms.

Further Illustrations of Expanding Collection Section 34

Yet another embodiment of the present invention is shown in FIGS. 8-18. Again, as the principal elements of this additional embodiments remain constant and similar to the previously discussed elements of the present invention, the discussions of those similar element(s) are expounded upon here. Later, attention is directed towards those aspects of the invention which slightly differ.

Various viewpoints of this embodiment in the first folded configuration are shown in FIGS. 8-11 and 13. FIGS. 12 and 14-18 illustrate various viewpoints of this embodiment in the second and third use configurations. As before, the expandable collection section 34 is defined by foldable portion 35 which in turn is generally comprised of portions of the side walls 23, 24, and the bottom wall 26.

In this embodiment, as before, the bottom wall 26 is folded inwards perpendicularly between the corners 29 when in the folded configuration. FIGS. 8-11 and 13 illustrate this, with FIG. 10 specifically showing the cross-sectional view illustrating how the bottom wall is folded inwards between corners 29.

Figure 13:
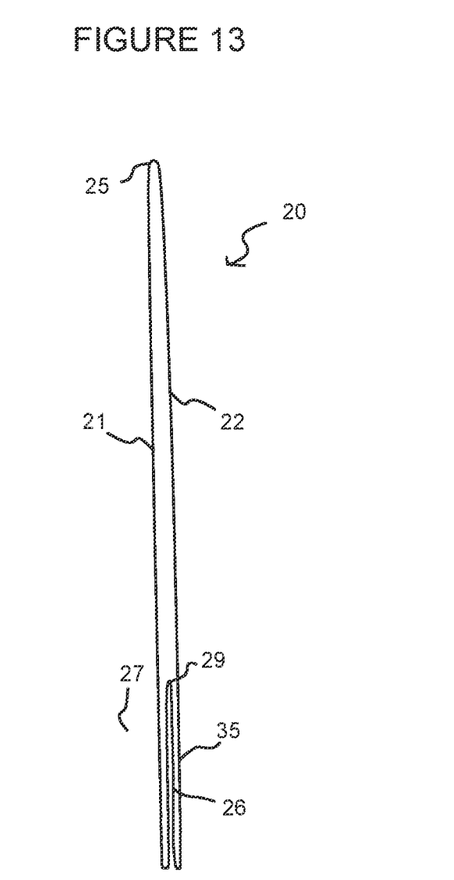
FIG. 13 is a side view of the first packing configuration of the embodiment shown in FIG. 8.
Figure 14:
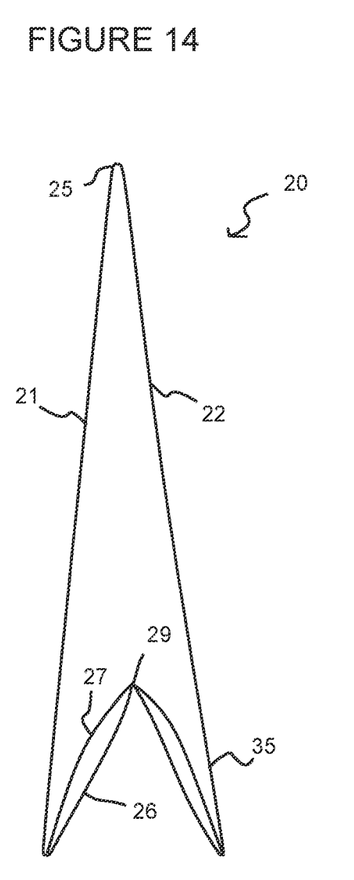
FIG. 14 is a side view of the embodiment in FIG. 8, also shown in the second use configuration.
Figure 15:
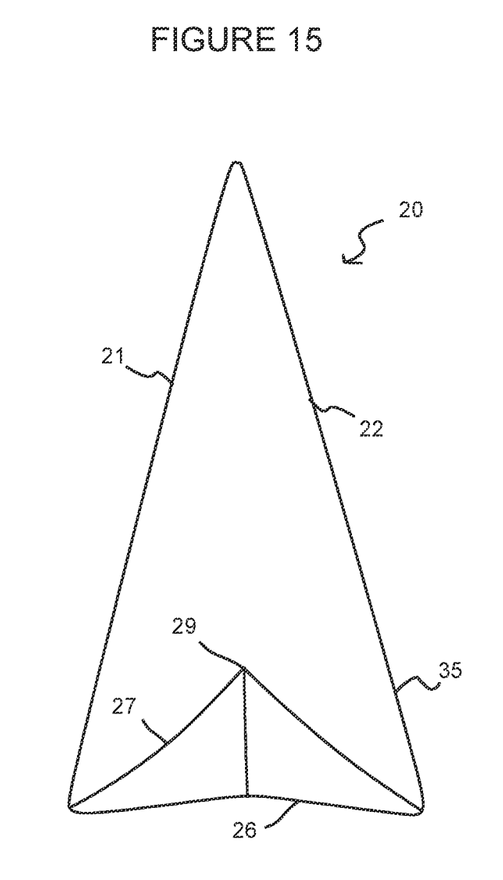
FIG. 15 is a side view of the embodiment in FIG. 8, shown in a third use configuration.
Figure 16:
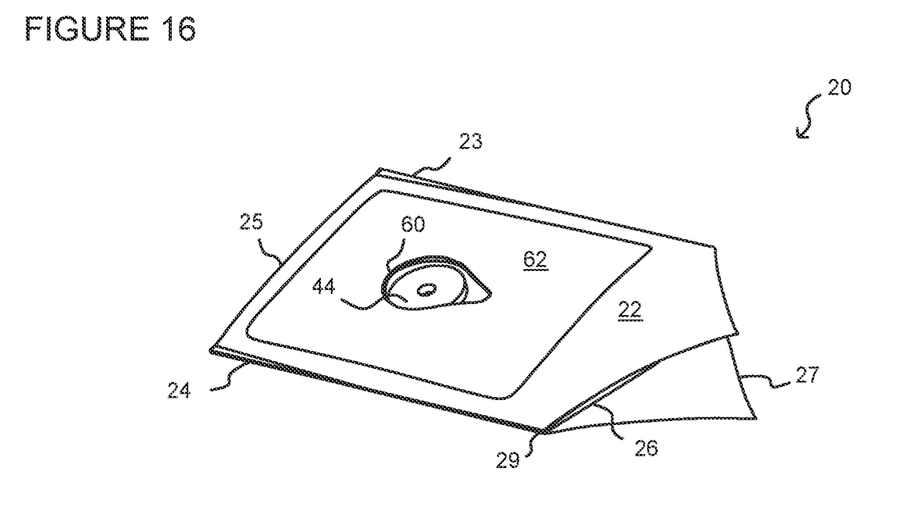
FIG. 16 is a rear perspective side view of the embodiment in FIG. 8, shown in the second use configuration.
Figure 17:
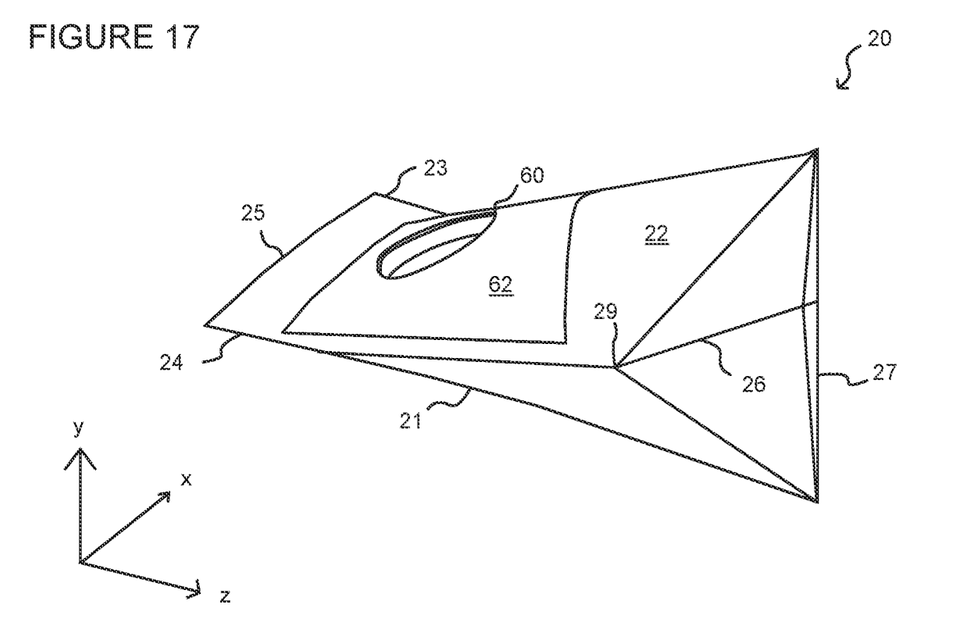
FIG. 17 is a rear perspective side view of the embodiment in FIG. 8, shown in the third use configuration.
Figure 18:
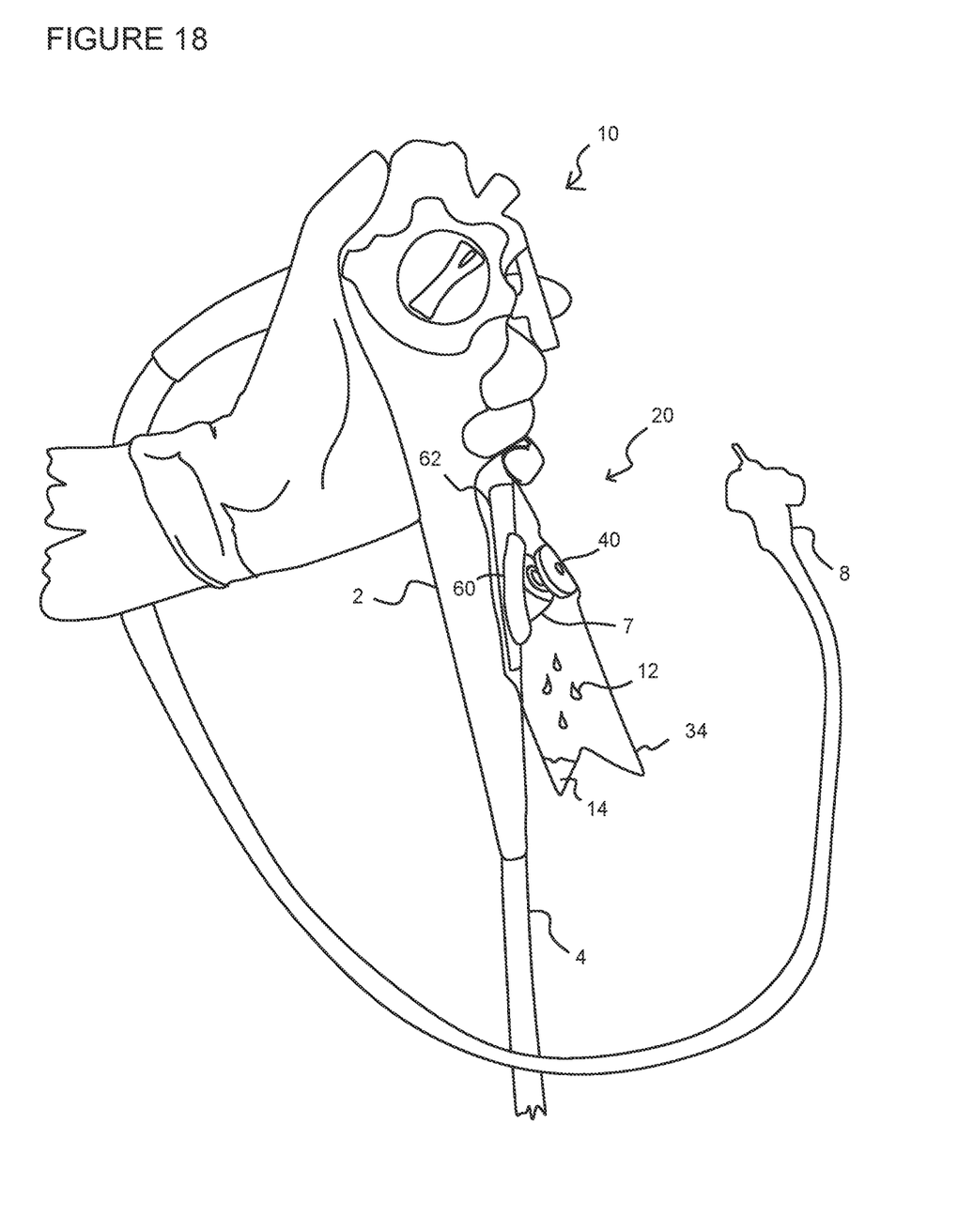
FIG. 18 is a side view of a transparent embodiment, shown in the second use configuration, during use and attached to an endoscope.

Note that when viewed from the front, the front wall 21 is an irregular hexagon in both configurations. However, as shown in FIGS. 13-15, when viewed from either of the sides, the shape changes from an extremely narrow rectangular shape (FIG. 13) to a first partially unfolded configuration in an arrowhead shape (FIG. 14) to a very bottom-heavy pyramidal (triangular) shape (FIG. 15).

As before, the overall volume increases significantly from the first configuration to the second configuration. This increase in volume is facilitated during manufacture by providing two seams along opposing perpendicular axes.

Figure 11:
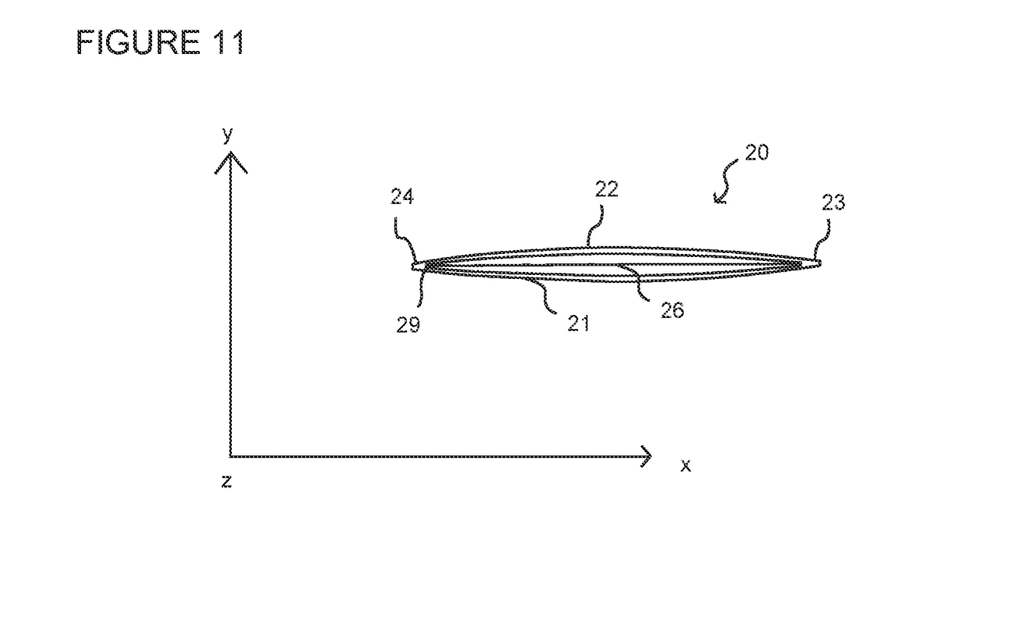
FIG. 11 is a bottom view of the embodiment in FIG. 8, shown in the first packing configuration.
Figure 12:
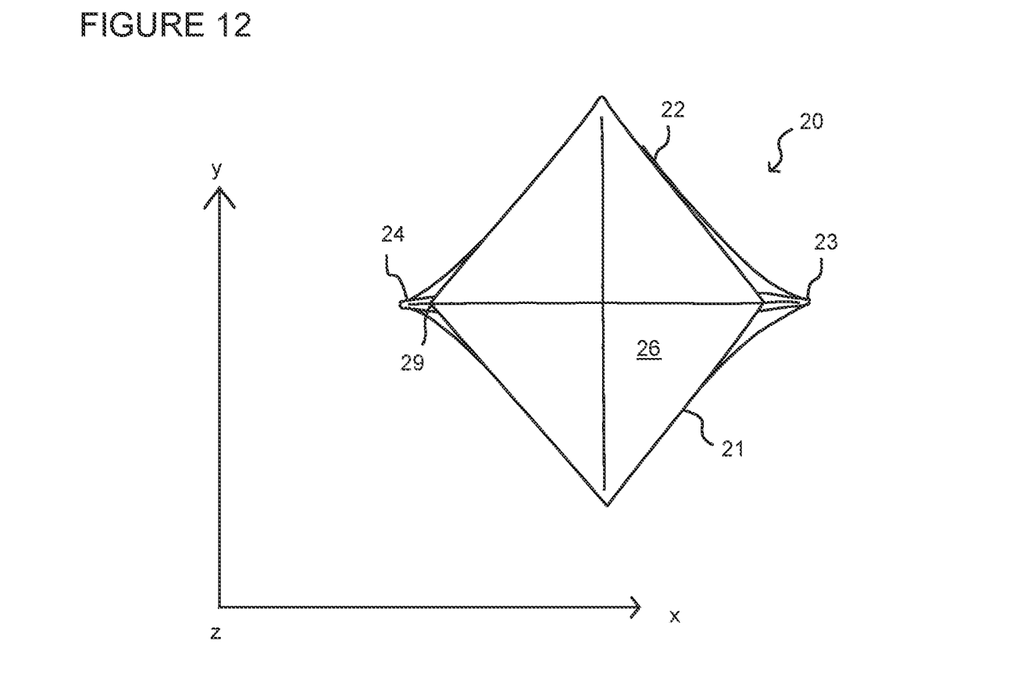
FIG. 12 is a bottom view of the embodiment in FIG. 8, shown in the second use configuration.

That is, in the folded first packing configuration, a first seam corresponding to the top wall 25 extends along the x-axis (FIG. 11). In the second use configuration, a second seam corresponding to the bottom wall 26 extends along the y-axis (FIG. 12).

Spill Proof Instrument Insertion Opening 40

In this embodiment, the outer ring 42 of the spill proof instrument insertion opening 40 is a colored and textured structure which provides additional protection and barrier against spilling while also providing additional support for the opening 40. The outer ring 42 in this embodiment is made from a foam material that is about 1 to 2 mm thick. The fenestration pattern 43 is similar, but the diameter is smaller, so that the inner diameter 44 of the outer ring is also smaller, about 5 mm.

Endoscope Attachment Aperture 60

The endoscope attachment aperture 60 of this embodiment is defined by a semi-circular, almost tear-drop shaped orifice 61 instead of a vertically extending rectangular slit as above. An upper portion of the aperture 60 is partially encompassed by an adjacent, but not abutting, arcuate brace 68. The brace 68 is made of a foam material that is about 1 to 2 mm thick an reduces the likelihood of fluid leakage around the endoscope attachment aperture 60.

Similar or identical in construction to the outer ring 42 of the spill proof instrument insertion opening 40, the brace 68 reduces spillage which might otherwise occur. However, instead of comprising a columnar portion, the arcuate brace 68 forms only about 70% of a circular circumference about the perimeter of the upper portion of the aperture 60. The brace 68 has a thickness which is equal to the thickness of the outer ring 42 so that these two components nest within each other when the container 20 is in the first folded configuration. The entire thickness of the container 20 in the first folded configuration then (FIG. 9) is not greater than 3 mm, and indeed is usually between 1-2 mm.

The wider shape of the outer facing portion of the orifice 66 along the upper portion facilitates engagement with wider endoscope instrument insertion portions 7 (see FIG. 11). The endoscope attachment aperture 60 also has a single large exterior adhesive strip 62 positioned along the back wall 22. This adhesive strip 62 has no vertically extending wings 64, however, it does have a larger surface area overall. When in the packing configuration as in FIG. 8, an adhesive cover 69 may be provided for transporting. This adhesive cover 69 may be provided without a matching orifice 66 in order to provide a sanitary seal for the fluid container 20 as a whole. However, it is also envisioned that a separate sanitary packaging could be provided for this purpose.

LIST OF REFERENCED ELEMENTS

The following reference numbers are adhered to within the specification to refer to those referenced elements within the drawings of the present application.

| | |
|---|---|
| 2 | handle |
| 4 | insertion tube |
| 7 | biopsy channel |
| 8 | endoscope instrument |
| 10 | endoscope |
| 12 | overspill of fluids |
| 14 | collected fluid |
| 20 | fluid container |
| 21 | front wall |
| 22 | back wall |
| 23 | left wall(s) |
| 24 | right wall(s) |
| 25 | top (wall) |
| 26 | bottom (wall) |
| 27 | bottom angled side wall(s) |
| 28 | upper corners |
| 29 | lower outer corners |
| 30 | collection sections |
| 31 | upper section |
| 32 | biopsy section |
| 33 | lower section |
| 34 | expandable collection section |
| 35 | foldable portion of side walls & bottom side walls |
| 36 | interior portion |
| 38 | transparent walls |
| 39 | top section (for calculating volume) |
| 40 | spill-proof instrument insertion opening |
| 41 | inner fenestrated membrane |
| 42 | outer ring |
| 43 | fenestration (cut) pattern |
| 44 | inner diameter |
| 45 | internal axis, center, focus |
| 46 | outer diameter |
| 50 | resealable drainage opening |
| 60 | endoscope attachment aperture |
| 61 | orifice |
| 62 | adhesive strip |
| 63 | adhesive strip |
| 64 | wing |
| 65 | wing |
| 66 | outer facing portion of orifice |
| 67 | integrated biopsy cap |
| 68 | arcuate brace |
| 69 | adhesive cover |

CONCLUSION

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

While the invention has been illustrated and described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

What is claimed is:

1. A fluid container for collecting fluids discharged from an endoscope, the endoscope having at least one instrument and at least one instrument channel, the fluid container comprising:

a front wall, a rear wall, a bottom wall, and side walls, wherein the front wall, the rear wall, the bottom wall, and the side walls are waterproof and define an interior portion of the fluid container, wherein the fluid container has a first volume and a second volume, and the side walls comprise upper side walls and lower side walls;

an expandable lower collection section and an upper section, the expandable lower collection section and the upper section being further defined by the front wall, the rear wall, the bottom wall, and the side walls, wherein the expandable lower collection section being capable of expanding, and the upper section having an upper portion, a main section, and a biopsy section, such that the fluid container alters shape from a first folded configuration to a second unfolded configuration, wherein the upper section has a depth of at least 4 mm in the first folded configuration and a depth of at least 40 mm in the second unfolded configuration, and wherein the expandable lower collection section has a triangular shape and the upper section has a rectangular shape in the first folded configuration, the rectangular shape of the upper section being defined by the upper side walls extending along a length of the fluid container from the front wall to the lower side walls of the expandable lower collection section, the lower side walls of the expandable lower collection section being angled; and the triangular shape of the expandable lower collection section being defined by the lower side walls extending from the upper side walls of the upper section to the bottom wall, and the expandable lower collection section and the upper section each has a triangular prism shape in the second unfolded configuration, wherein the fluid container has the second volume when the fluid container is in the second unfolded configuration and the first volume when the fluid container is in the first folded configuration, and the second volume is between 2 to 10 times greater than the first volume;

a first opening, which facilitates insertion of the at least one instrument through an orifice of the first opening into the fluid container, wherein the first opening being located on the front wall of the fluid container; and a second opening, which facilitates egression of the at least one instrument inserted through the first opening to exit the fluid container, wherein the second opening is adapted to be fitted over the at least one instrument channel of the endoscope, and further being adapted to facilitate such egression of the at least one instrument into the at least one instrument channel of the endoscope.

2. The fluid container of claim 1 wherein the front wall, the rear wall, the bottom wall, and the side walls of the fluid container are substantially transparent so that the interior portion can be visualized from outside the fluid container.

3. The fluid container of claim 1 further comprising a marker located around the first opening capable of providing a visual and tactile target to help a user identify the orifice of the first opening.

4. The fluid container of claim 1 further comprising a spill-proof seal covering the orifice of the first opening to facilitate reduction of overspill of fluids through the first opening.

5. The fluid container of claim 4 wherein the spill-proof seal covering the orifice of the first opening comprising a fenestrated membrane.

6. The fluid container of claim 4 wherein the spill-proof seal covering the orifice of the first opening comprising a first fenestrated membrane having a first fenestration pattern and a second fenestrated membrane having a second fenestration pattern.

7. The fluid container of claim 1 further comprising a self-adhesive band around the second opening as a means for attaching the fluid container to the endoscope.

8. The fluid container of claim 1 further comprising an integrated rubber seal located adjacent the second opening as a means for connecting the fluid container to the instrument channel of the endoscope.

9. The fluid container of claim 1 further comprising a third opening, being adapted to permit fluids collected within the fluid container to be removed from the fluid container without removal of the at least one instrument from the orifice of the first opening into the fluid container.

10. The fluid container of claim 9 wherein the third opening being located adjacent the bottom wall of the fluid container.

11. The fluid container of claim 10 further comprising a water-tight sealing mechanism connected to the third opening; wherein the sealing mechanism facilitates the third opening in opening and closing repeatedly.

12. The fluid container of claim 11 wherein the water-tight sealing mechanism is a zipper connected to the third opening; wherein the zipper facilitates the third opening in opening and closing repeatedly.

13. The fluid container of claim 1, wherein the front wall, the rear wall, the bottom wall, and the side walls are folded portions of a single sheet of thin layer of medical grade plastic sheeting.

14. The fluid container of claim 13, wherein the medical grade plastic sheeting is selected from a group consisting of plastic, silicone, rubber, and cellulose.

15. A fluid container for collecting fluids discharged from an endoscope, the endoscope having at least one instrument and at least one instrument channel, the fluid container comprising:

at least one folded waterproof wall defining an interior portion of the fluid container;

an instrument insertion opening being adapted to facilitate insertion of the at least one instrument therethrough into the fluid container, the instrument insertion opening being located on an exterior facing portion of the at least one folded water-proof wall of the fluid container;

an endoscope attachment aperture being adapted to be fitted over the at least one instrument channel of the endoscope, the endoscope attachment aperture being adapted to facilitate egression of the at least one instrument, inserted through the instrument insertion opening, to exit the fluid container and enter the at least one instrument channel of the endoscope;

an expandable lower collection section being capable of collecting the fluids discharged from the at least one instrument channel of the endoscope, and an upper section, the upper section having an upper portion, main section, and biopsy section;

a first packing configuration having a first volume, wherein the expandable lower collection section has a triangular shape and the upper section has a rectangular shape in the first packing configuration, the expandable lower collection section and the upper section being further defined by a front wall, a rear wall, a bottom wall, and side walls, wherein the side walls comprise upper side walls and lower side walls, the rectangular shape of the upper section being defined by the upper side walls extending along a length of the fluid container from the front wall to the lower side walls of the expandable lower collection section, the lower side walls of the expandable lower collection section being angled; and the triangular shape of the expandable lower collection section being defined by the lower side walls extending from the upper side walls of the upper section to the bottom wall; and a second collecting configuration having a second volume, wherein the expandable lower collection section and the upper section each has a triangular prism shape in the second configuration;

wherein the upper section has a depth of at least 4 mm in the first folded configuration and a depth of at least 40 mm in the second collecting configuration, and the second volume of the second collecting configuration is between 2 to 10 times greater than the first volume of the first packing configuration; and wherein the fluid container being reversibly collapsible and expandable from the first packing configuration to the second collecting configuration.

16. The fluid container of claim 15 wherein the second volume of the second collecting configuration is at least five times greater than the first volume of the first packing configuration.

17. The fluid container of claim 15 further comprising a first manufacturing seam along a first axis, and a second opposing manufacturing seam along a second axis, wherein the first axis is perpendicular to the second axis.

18. The fluid container of claim 1, wherein the upper section has a height that is the height of the upper portion plus the height of the biopsy section plus the height of the main section minus the height of the expandable lower collection section in the first folded configuration.

19. The fluid container of claim 1, wherein the depth of the fluid container in the first folded configuration is less than the depth of the fluid container in the second unfolded configuration.

20. The fluid container of claim 1, wherein the volume of the expandable lower collection section is greater than the volume of the upper section in the second unfolded configuration.

* * * * *